(12) United States Patent
Skalla et al.

US012139577B2

(10) Patent No.: US 12,139,577 B2
(45) Date of Patent: *Nov. 12, 2024

(54) BIODEGRADABLE TRIBLOCK COPOLYMERS AND IMPLANTABLE MEDICAL DEVICES MADE THEREFROM

(71) Applicants: Covidien LP, Mansfield, MA (US); SOFRADIM PRODUCTION, Trevoux (FR)

(72) Inventors: Walter Skalla, Old Lyme, CT (US); Jonathan Thomas, New Haven, CT (US); Thierry Brune, Jarnioux (FR); Darlene P. Nebinger, Oxford, CT (US); Seth S. Gleiman, Guilford, CT (US); Robert Vestberg, Charbonniere les Bains (FR)

(73) Assignees: SOFRADIM PRODUCTION, Trevoux (FR); Covidien LP, Mansfield, MA (US)

( * ) Notice: Subject to any disclaimer, the term of this patent is extended or adjusted under 35 U.S.C. 154(b) by 44 days.

This patent is subject to a terminal disclaimer.

(21) Appl. No.: 17/949,176

(22) Filed: Sep. 20, 2022

(65) Prior Publication Data
US 2023/0028641 A1  Jan. 26, 2023

Related U.S. Application Data

(63) Continuation of application No. 16/582,151, filed on Sep. 25, 2019, now Pat. No. 11,447,602.

(30) Foreign Application Priority Data

Sep. 26, 2018 (EP) ..................... 18197009
Dec. 5, 2018 (EP) ..................... 18210563

(51) Int. Cl.
| | | |
|---|---|---|
| *A61K 31/765* | (2006.01) | |
| *A61L 15/64* | (2006.01) | |
| *A61L 17/12* | (2006.01) | |
| *A61L 27/18* | (2006.01) | |
| *A61L 27/58* | (2006.01) | |
| *A61L 31/06* | (2006.01) | |
| *A61L 31/14* | (2006.01) | |
| *C08G 63/64* | (2006.01) | |
| *C08G 63/85* | (2006.01) | |

(52) U.S. Cl.
CPC ............. *C08G 63/64* (2013.01); *A61L 17/12* (2013.01); *A61L 27/18* (2013.01); *A61L 27/58* (2013.01); *A61L 31/06* (2013.01); *A61L 31/148* (2013.01); *C08G 63/85* (2013.01); *C08G 2230/00* (2013.01)

(58) Field of Classification Search
CPC ........ A61L 17/12; A61L 15/64; A61K 31/765
USPC ..................................... 424/78.38, 426, 444
See application file for complete search history.

(56) References Cited

U.S. PATENT DOCUMENTS

| | | |
|---|---|---|
| 3,639,503 A | 2/1972 | Matzner |
| 4,300,565 A | 11/1981 | Rosensaft et al. |
| 4,429,080 A | 1/1984 | Casey et al. |
| 4,705,820 A | 11/1987 | Wang et al. |
| 4,711,241 A | 12/1987 | Lehmann |
| 4,716,203 A | 12/1987 | Casey et al. |
| 4,788,979 A | 12/1988 | Jarrett et al. |
| 4,791,929 A | 12/1988 | Jarrett et al. |
| 4,891,263 A | 1/1990 | Kotliar et al. |
| 5,185,408 A | 2/1993 | Tang et al. |
| 5,252,701 A | 10/1993 | Jarrett et al. |
| 5,256,762 A | 10/1993 | Hermes et al. |
| 5,320,624 A | 6/1994 | Kaplan et al. |
| 5,322,925 A | 6/1994 | Muth et al. |
| 5,403,347 A | 4/1995 | Roby et al. |
| 5,431,679 A | 7/1995 | Bennett et al. |
| 5,475,063 A | 12/1995 | Kaplan et al. |
| 5,522,841 A | 6/1996 | Roby et al. |
| 5,531,998 A | 7/1996 | Mares et al. |
| 5,554,170 A | 9/1996 | Roby et al. |
| 6,083,524 A | 7/2000 | Sawhney et al. |
| 6,093,792 A | 7/2000 | Gross et al. |
| 6,177,095 B1 | 1/2001 | Sawhney et al. |
| 6,191,236 B1 | 2/2001 | Roby et al. |
| 6,206,908 B1 | 3/2001 | Roby |

(Continued)

FOREIGN PATENT DOCUMENTS

| | | |
|---|---|---|
| EP | 0460428 A2 | 12/1991 |
| EP | 0460439 A2 | 12/1991 |

(Continued)

OTHER PUBLICATIONS

Notice of Reasons for Rejection issued in Japanese Patent Application No. 2019154508 dated Aug. 16, 2023 with English translation.

(Continued)

*Primary Examiner* — Raymond J Henley, III
(74) *Attorney, Agent, or Firm* — Weber Rosselli & Cannon LLP (57) ABSTRACT

A biodegradable triblock copolymer comprising: an A-B-A' structure wherein the A and A' blocks each include polylactide, the B block includes from about 55 to about 100 mole percent of polytrimethylene carbonate and 0 to about 45 mole percent polylactide, and the biodegradable triblock copolymer overall includes from about 15 to about 25 mole percent of the polytrimethylene carbonate and from about 75 to about 85 mole percent of the polylactide. Also provided are compositions and implantable medical devices made therefrom.

19 Claims, 6 Drawing Sheets

(56) References Cited

U.S. PATENT DOCUMENTS

| | | |
|---|---|---|
| 6,228,954 B1 | 5/2001 | Kaplan et al. |
| 6,273,897 B1 | 8/2001 | Dalessandro et al. |
| 6,316,581 B1 | 11/2001 | Gross et al. |
| RE39,713 E | 7/2007 | Sawhney et al. |
| 9,364,442 B2 | 6/2016 | Steendam et al. |
| 9,605,112 B2 | 3/2017 | Kohn et al. |
| 11,447,602 B2 * | 9/2022 | Skalla .................. A61L 31/148 |
| 2008/0243228 A1 | 10/2008 | Wang et al. |
| 2013/0274422 A1 | 10/2013 | Carpentier et al. |

FOREIGN PATENT DOCUMENTS

| | | |
|---|---|---|
| EP | 0722966 A2 | 7/1996 |
| EP | 2358785 B1 | 2/2016 |
| JP | H04226527 A | 8/1992 |
| JP | H04231963 A | 8/1992 |
| JP | H08295730 A | 11/1996 |
| JP | 2010532216 A | 10/2010 |
| JP | 2014525487 A | 9/2014 |
| PL | 22669 B1 | 8/2016 |
| WO | 2009005909 A2 | 1/2009 |
| WO | 2013030324 A1 | 3/2013 |

OTHER PUBLICATIONS

Fabrication of Totally Biodegradable Cardiac Occluders From Biodegradable Copolyesters, Tang Baiyu, "China Master's Theses Full-text Database Engineering Science and Technology II", Jan. 15, 2018, No. 01, pages C030-45 with English translation.

Notification of the Second Office Action issued in Chinese Patent Application No. 201910905734.7 dated Apr. 5, 2023 with English translation.

Communication pursuant to Article 94(3) EPC issued in European Application No. 18210563.5 dated Nov. 25, 2021.

Extended European Search Report issued in European Application No. 18210563.5 dated Sep. 11, 2019, 6 pages.

* cited by examiner

FIG. 8

BIODEGRADABLE TRIBLOCK COPOLYMERS AND IMPLANTABLE MEDICAL DEVICES MADE THEREFROM

CROSS-REFERENCE TO RELATED APPLICATIONS

This application is a continuation of U.S. patent application Ser. No. 16/582,151 filed Sep. 25, 2019, which claims benefit of and priority to European Patent Application Serial No. 18197009.6 filed Sep. 26, 2018 and European Patent Application Serial No. 18210563.5 filed Dec. 5, 2018, the disclosures of each of the above-identified applications are hereby incorporated by reference in their entirety.

TECHNICAL FIELD

The present disclosure relates to biodegradable triblock copolymers and implantable medical devices made therefrom, and particularly, ABA' triblock copolymers including polylactic acid and polytrimethylene carbonate.

BACKGROUND

Implantable medical devices including filaments made from pure polylactic acid (PLA) are known. Pure PLA is considered beneficial as a long term biodegradable material suitable for implantation with enhanced strength. However, pure PLA can also be very brittle and/or stiff to work with thereby making it difficult to extrude and/or spin into filaments. In addition, when successfully formed into filaments, pure PLA filaments can be prone to premature failure when stressed because of their brittle and/or stiff nature. The failure being premature because the failure or break can occur well before the pure PLA material has been fully degraded. For example, pure PLA filaments can take 12 months or longer to fully degrade at 37° C. (body temperature) but may fail between 6 and 12 months at 37° C. rendering the broken pure PLA filaments significantly less effective long term. It would be advantageous to provide a biodegradable material suitable for filament formation which provides better long term persistence and better handling and strength characteristics than pure PLA.

SUMMARY

The present disclosure describes biodegradable triblock copolymers including an A-B-A' structure wherein the A and A' blocks each include polylactide or polylactic acid, the B block includes from about 55 to about 100 mole percent of polytrimethylene carbonate and 0 to about 45 mole percent polylactide or polylactic acid, and the biodegradable triblock copolymer overall includes from about 15 to about 25 mole percent of the polytrimethylene carbonate and from about 75 to about 85 mole percent of the polylactide or polylactic acid.

In addition, the present disclosure describes compositions including at least one of the biodegradable triblock copolymers described herein and at least one additional biocompatible material, wherein the biodegradable triblock copolymer is of the structure A-B-A', wherein the A and A' blocks each include polylactide or polylactic acid, the B block includes from about 55 to about 100 mole percent of polytrimethylene carbonate and about 0 to about 45 mole percent polylactide or polylactic acid, and the biodegradable triblock copolymer overall includes from about 15 to about 25 mole percent of the polytrimethylene carbonate and from about 75 to about 85 mole percent of the polylactide or polylactic acid.

The biodegradable ABA' triblock copolymers described herein, alone or in one of the compositions described herein, are further described as being formed into implantable medical devices and particularly fibrous implantable medical devices.

Particularly, the present disclosure describes an implantable medical device including at least one filament made of a biodegradable triblock copolymer including an A-B-A' structure wherein the A and A' blocks each include polylactide or polylactic acid, the B block includes from about 55 to about 100 mole percent of polytrimethylene carbonate and about 0 to about 45 mole percent polylactide or polylactic acid, and the biodegradable triblock copolymer overall includes from about 15 to about 25 mole percent of the polytrimethylene carbonate and from about 75 to about 85 mole percent of the polylactide or polylactic acid.

The present disclosure also describes an implantable medical device including at least one filament made of a composition including a biodegradable triblock copolymer and an additional biocompatible material, the triblock copolymer including an A-B-A' structure wherein the A and A' blocks each include polylactide or polylactic acid, the B block includes from about 55 to about 100 mole percent of polytrimethylene carbonate and about 0 to about 45 mole percent polylactide or polylactic acid, and the biodegradable triblock copolymer overall includes from about 15 to about 25 mole percent of the polytrimethylene carbonate and from about 75 to about 85 mole percent of the polylactide or polylactic acid.

Methods of forming the biodegradable triblock copolymers described herein and the implantable medical devices including the triblock copolymers are also provided.

DETAILED DESCRIPTION

The present disclosure describes biodegradable ABA' triblock copolymers including polylactic acid and polytrimethylene carbonate. The biodegradable ABA' triblock copolymers being suitable for forming compositions and implantable medical devices, in particular medical devices including filaments. Methods of forming the biodegradable ABA' triblock copolymers are also described.

The term "ABA' triblock copolymer(s)" is defined herein as a block copolymer having moieties A, B and A' arranged according to the general formula $-\{[A\text{-}]_a\text{-}[B]_b\text{-}[A']_{a'}\}_{\text{-}d}$, where each of "a," "b," "a'" and "d" independently is greater than or equal to ($\geq$) 1. For example, each of "a," "b," "a'," and "d" may independently range from 1 to 1,000. In embodiments, each "a," "b," "a'," and "d" may independently range from about 1 to 600. In embodiments, each "a," "b," "a'," and "d" may independently range from about 2 to 300. In embodiments, each "a," "b," "a'," and "d" may independently range from about 5 to 125.

In some embodiments, each "a" and "a'" may independently range from about 100 to about 500. In embodiments, each "a" and "a'" may independently range from about 150 to about 400. In embodiments, each "a" and "a'" may independently range from about 200 to about 300.

In some embodiments, each "a" and "a'" may be about the same number ranging from about 100 to about 500. In embodiments, each "a" and "a'" may be about the same number ranging from about 150 to about 400. In embodiments, each "a" and "a'" may be about the same number ranging from about 200 to about 300.

In some embodiments, "b" may range from about 200 to about 800. In embodiments, "b" may range from about 300 to about 700. In embodiments, "b" may range from about 400 to about 600.

In some embodiments, each "a" and "a'" may independently range from about 100 to about 500 and "b" may range from about 200 to about 800.

In some embodiments, each "a" and "a'" may be about the same number ranging from about 100 to about 500 and "b" may range from about 200 to about 800.

In some embodiments, each "a" and "a'" may independently range from about 150 to about 400 and "b" may range from about 300 to about 700.

In some embodiments, each "a" and "a'" may be about the same number ranging from about 150 to about 400 and "b" may range from about 300 to about 700.

In some embodiments, each "a" and "a'" may independently range from about 200 to about 300 and "b" may range from about 400 to about 600.

In some embodiments, each "a" and "a'" may be about the same number ranging from about 200 to about 300 and "b" may range from about 400 to about 600.

In addition, any ranges provided herein are intended to encompass the entire range inclusively, including not only the starting and ending number of the range but also any whole number or fraction of a number which falls within the range, individually or in any combination of narrower ranges. For example, a B block including 80 to 100 mole percent polytrimethylene carbonate (pTMC) and 0 to 20 mole percent polylactide or polylactic acid (PLA) may include pTMC/PLA in the following: individual whole number ratios, such as 80/20, 81/19, 82/18, 83/17, 84/16, 85/15, 86/14, 87/13, 88/12, 89/11, 90/10, 91;9, 92/8, 93/7, 94/6, 95/5, 96/4, 97/3, 98/2, 99/1, and 100/0; individual fractional number ratios, such as the following non-limiting examples, 82.5/17.5, 83.25/16.75, 85.3/14.7, 91.4/8.6, 99.7/0.3, and the like; or narrower ranges, such as the following non-limiting examples, 81 to 99 mole percent pTMC and 1 to 19 mole percent PLA or 84.5 to 93.6 mole percent pTMC and 6.4 to 15.5 mole percent PLA, etc.

The present disclosure describes biodegradable ABA' triblock copolymers wherein the A and A' blocks each include polylactide or polylactic acid, the B block includes from about 55 to about 100 mole percent of polytrimethylene carbonate and about 0 to about 45 mole percent polylactide or polylactic acid, and the biodegradable triblock copolymer overall includes from about 15 to about 25 mole percent of the polytrimethylene carbonate and from about 75 to about 85 mole percent of the polylactide or polylactic acid.

The A and A' blocks of the ABA' triblock copolymers described herein each independently include polylactide or polylactic acid. In embodiments, the A and A' blocks consist or consist essentially of polylactide or polylactic acid. In other embodiments, up to about 10 mol %, 20 mol %, 30 mol % or 40 mol % of other monomer units may be present.

The terms "polylactide" and "polylactic acid" are used interchangeably throughout the present disclosure. To the extent "polylactide" and "polylactic acid" may be interpreted differently, each of the embodiments described herein may include "polylactide", "polylactic acid" or both. The terms "polylactide" and "polylactic acid" refer to polymers comprising residues obtainable by polymerization of lactide, that is to say polymer residues of formula $-\text{OCH}(\text{CH}_3)\text{COOCH}(\text{CH}_3)\text{CO}-$ as shown in Formula (I) below. The term "polytrimethylene carbonate" refers to polymers containing residues obtainable by polymerization of trimethylene carbonate, that is to say residues of formula $-\text{OCH}_2\text{CH}_2\text{CH}_2\text{OCO}-$ as shown in Formula (I) below. The mole percentages of polylactide/polyglycolide or polytrimethylene carbonate recited herein refer to the mole percentages of residues of formula $\text{OCH}(\text{CH}_3)\text{COOCH}(\text{CH}_3)\text{CO}-$ as shown in Formula (I) below or $-\text{OCH}_2\text{CH}_2\text{CH}_2\text{OCO}-$ as shown in Formula (I) below, respectively, in the polymers of the invention.

There are several different types of polylactide and/or polylactic acid polymers including poly-L-lactic acid (PLLA), poly-D-lactic acid (PDLA), and combinations and/or racemic versions of both, such as poly-DL-lactic acid (PDLLA). The A and A' blocks of the ABA' triblock copolymers described herein each independently include at least one type of polylactic acid. In some embodiments, the A and A' blocks include the same type of polylactic acid. In some embodiments, the A and A' blocks include different types of polylactic acid.

The B block of the ABA' triblock copolymers described herein includes from about 55 to about 100 mole percent polytrimethylene carbonate and 0 to about 45 mole percent polylactic acid. The B block may be a random copolymer of polytrimethylene carbonate and polylactic acid in these mole percent ranges. Suitably, the B block of the ABA' triblock copolymers consists or consists essentially of the polytrimethylene carbonate and polylactic acid monomer units, substantially free from other monomer units. In embodiments, up to about 10 mol %, 20 mol. %, 30 mol % or 40 mol % of other monomer units may be present.

In some embodiments, the B block of the ABA' triblock copolymers described herein include from about 55 to about 95 mole percent polytrimethylene carbonate and about 5 to about 45 mole percent polylactic acid.

In some embodiments, the B block of the ABA' triblock copolymers described herein include from about 85 to about 95 mole percent polytrimethylene carbonate and about 5 to about 15 mole percent polylactic acid.

In some embodiments, the A and A' blocks are both pure polylactic acid and the B block is a random copolymer of polytrimethylene carbonate and polylactic acid.

In some particular embodiments, the B block includes about 100 mole percent polytrimethylene carbonate and about 0 mole percent polylactic acid.

In some particular embodiments, the B block includes about 95 mole percent polytrimethylene carbonate and about 5 mole percent polylactic acid In some particular embodiments, the B block includes about 90 mole percent polytrimethylene carbonate and about 10 mole percent polylactic acid.

In some particular embodiments, the B block includes about 85 mole percent polytrimethylene carbonate and about 15 mole percent polylactic acid.

In some particular embodiments, the B block includes about 80 mole percent polytrimethylene carbonate and about 20 mole percent polylactic acid.

In some particular embodiments, the B block includes about 75 mole percent polytrimethylene carbonate and about 25 mole percent polylactic acid.

In some particular embodiments, the B block includes about 70 mole percent polytrimethylene carbonate and about 30 mole percent polylactic acid.

In some particular embodiments, the B block includes about 65 mole percent polytrimethylene carbonate and about 35 mole percent polylactic acid.

In some particular embodiments, the B block includes about 60 mole percent polytrimethylene carbonate and about 40 mole percent polylactic acid.

In some particular embodiments, the B block includes about 55 mole percent polytrimethylene carbonate and about 45 mole percent polylactic acid.

While the B block of the biodegradable ABA' triblock copolymers described herein is predominantly polytrimethylene carbonate, the ABA' triblock copolymer(s) overall, i.e., including all 3 blocks A, B, and A', is predominantly polylactic acid. By predominantly, the material represents greater than or equal to 75 mole percent of the block, i.e., the B block and/or the overall triblock. In some embodiments, the ABA' triblock copolymer(s) are overall predominantly polylactic acid while including a B block which is predominantly polytrimethylene carbonate.

In embodiments, the biodegradable ABA' triblock copolymers overall may include from about 15 to about 25 mole percent of the polytrimethylene carbonate and from about 75 to about 85 mole percent of the polylactic acid.

In embodiments, the biodegradable ABA' triblock copolymer overall includes only from about 15 to about 25 mole percent of the polytrimethylene carbonate and from about 75 to about 85 mole percent of the polylactic acid.

In some embodiments, the biodegradable ABA' triblock copolymer overall includes about 15 mole percent polytrimethylene carbonate and about 85 mole percent polylactic acid In some embodiments, the biodegradable ABA' triblock copolymer overall includes about 20 mole percent polytrimethylene carbonate and about 80 mole percent polylactic acid.

In some embodiments, the biodegradable ABA' triblock copolymer overall includes about 25 mole percent polytrimethylene carbonate and about 75 mole percent polylactic acid.

In some particular embodiments, the biodegradable ABA' triblock copolymer are described wherein the A and A' blocks each include polylactic acid, the B block includes about 100 mole percent of polytrimethylene carbonate and 0 mole percent polylactic acid, and the biodegradable triblock copolymer overall includes about 20 mole percent of the polytrimethylene carbonate and about 80 mole percent of the polylactic acid.

In some particular embodiments, the biodegradable ABA' triblock copolymer are described wherein the A and A' blocks each include polylactic acid, the B block includes about 95 mole percent of polytrimethylene carbonate and 5 mole percent polylactic acid, and the biodegradable triblock copolymer overall includes about 20 mole percent of the polytrimethylene carbonate and about 80 mole percent of the polylactic acid.

In some particular embodiments, the biodegradable ABA' triblock copolymer are described wherein the A and A' blocks each include polylactic acid, the B block includes about 90 mole percent of polytrimethylene carbonate and 10 mole percent polylactic acid, and the biodegradable triblock copolymer overall includes about 20 mole percent of the polytrimethylene carbonate and about 80 mole percent of the polylactic acid.

In some particular embodiments, the biodegradable ABA' triblock copolymer are described wherein the A and A' blocks each include polylactic acid, the B block includes about 85 mole percent of polytrimethylene carbonate and 15 mole percent polylactic acid, and the biodegradable triblock copolymer overall includes about 20 mole percent of the polytrimethylene carbonate and about 80 mole percent of the polylactic acid.

In some particular embodiments, the biodegradable ABA' triblock copolymer are described wherein the A and A' blocks each include polylactic acid, the B block includes about 80 mole percent of polytrimethylene carbonate and 20 mole percent polylactic acid, and the biodegradable triblock copolymer overall includes about 20 mole percent of the polytrimethylene carbonate and about 80 mole percent of the polylactic acid.

In some particular embodiments, the biodegradable ABA' triblock copolymer are described wherein the A and A' blocks each include polylactic acid, the B block includes about 70 mole percent of polytrimethylene carbonate and 30 mole percent polylactic acid, and the biodegradable triblock copolymer overall includes about 20 mole percent of the polytrimethylene carbonate and about 80 mole percent of the polylactic acid.

In some particular embodiments, the biodegradable ABA' triblock copolymer are described wherein the A and A' blocks each include polylactic acid, the B block includes about 55 mole percent of polytrimethylene carbonate and 45 mole percent polylactic acid, and the biodegradable triblock copolymer overall includes about 20 mole percent of the polytrimethylene carbonate and about 80 mole percent of the polylactic acid.

In all of the above definitions, references to the ABA' block copolymer including specified amounts of polylactide and/or trimethylene carbonate suitably refer to the copolymer block consisting essentially of or consisting of these components.

The biodegradable ABA' triblock copolymer(s) described herein display a melting temperature ($T_m$) ranging from about 160° C. to about 185° C. In embodiments, the copolymers described herein display a Tm ranging from about 165° C. to about 180° C. In embodiments, the copolymers described herein display a Tm ranging from about 170° C. to about 175° C.

The biodegradable ABA' triblock copolymer(s) described herein display a glass transition temperature ($T_g$) ranging from about 40° C. to about 65° C. In embodiments, the copolymers described herein display a Tg ranging from about 45° C. to about 60° C. In embodiments, the copolymers described herein display a Tg ranging from about 52° C. to about 57° C.

For forming filaments and/or medical devices, the triblock copolymer(s) described herein need to have sufficient molar mass, i.e., weight average molecular weight (Mw) and/or number average molecular weight (Mn). Accordingly, in some embodiments, optionally in combination with one or more other embodiments described herein, the triblock copolymers have a molecular weight ($M_w$) of at least about 100,000 g/mol. In some embodiments, the triblock copolymers have an Mw of at least about 150,000 g/mol. In some embodiments, the triblock copolymers have an Mw of at least about 180,000 g/mol.

In some embodiments, optionally in combination with one or more other embodiments described herein, the triblock copolymers range in Mw from about 150,000 g/mol to about 225,000 g/mol. In other embodiments, the triblock copolymers range in Mw from about 160,000 g/mol to about 215,000 g/mol. In still other embodiments, the triblock copolymers range in Mw from about 175,000 g/mol to about 210,000 g/mol. In yet other embodiments, the triblock copolymers range in Mw from about 170,000 g/mol to about 190,000 g/mol.

In some embodiments, optionally in combination with one or more other embodiments described herein, the triblock copolymers have a polymer number-average molecular weight ($M_n$) of at least about 100,000 g/mol. In some embodiments, the triblock copolymers have a $M_n$ of at least about 110,000 g/mol.

In some embodiments, optionally in combination with one or more other embodiments described herein, the triblock copolymers range in $M_n$ from about 100,000 g/mol to about 150,000 g/mol. In some embodiments, the triblock copolymers range in $M_n$ from about 110,000 g/mol to about 140,000 g/mol. In some embodiments, the triblock copolymers range in $M_n$ from about 112,000 g/mol to about 130,000 g/mol. In some embodiments, the triblock copolymers range in $M_n$ from about 115,000 g/mol to about 125,000 g/mol. In some embodiments, the triblock copolymers range in $M_n$ from about 100,000 g/mol to about 120,000 g/mol.

Biodegradable triblock copolymers of the present disclosure having a $M_w$ and a $M_n$ from about 100,000 g/mol to about 225,000 g/mol may be more suitable for forming filaments and/or medical devices. In some embodiments, the biodegradable triblock copolymers of the present disclosure have a $M_w$ and a $M_n$ from about 110,000 g/mol to about 210,000 g/mol In some embodiments, the biodegradable triblock copolymers of the present disclosure have a $M_w$ and a $M_n$ ratio, i.e., polydisperse index (PDI), ranging from 1.4:1 to 1.75:1, in some embodiments from 1.5:1 to 1.65:1, for being processed into filaments and/or medical devices.

The $M_w$, $M_n$, and PDI of the ABA' triblock copolymers described herein may be determined using size-exclusion chromatography (SEC). For example, in some embodiments, absolute molar mass measurements can be performed using a chromatography system such as Waters APC (Advanced polymer chromatography system, Waters Corporation, Milford, USA) with light scattering and RI detection. Such systems may operate using various solvents, including but not limited to HFIP (1,1,1,3,3,3-hexafluoro-2-propanol) and at various temperatures. Analysis can be performed in some instances at a temperature of about 40 C, with an injection volume of about 30 µl, a flow rate of about 0.3 mL/min and a sample concentration of about 1.5 mg/ml. In some instances, the systems may include columns from Agilent Technologies (Santa Clara, CA, USA) such as columns PL HFIP gel Guard 50*4.6 mm and/or columns PL HFIP gel 250*4.6 mm. In some instances, the systems may include an RI detector such as Optilab T-rEX from Wyatt technologies (Santa Barbara, CA, USA) and/or a multi-angle light scattering detector Dawn Heleos II (wavelength of 660.4 nm) also from Wyatt technologies. The light scattering measurements and the RI measurements may be calculated using Astra 6.1.7 software also from Wyatt technologies.

The $T_m$ and $T_g$ of the ABA' triblock copolymers described herein may be determined using differential scanning calorimetry (DSC). For example, in some embodiments, DSC measurements can be carried out on a Mettler Toledo DSC thermal analyzer, integrated with software STARe. In some instances, for each of the references measured, five samples (5-6 mg) were submitted to a heating scan to 200° C. (10° C./min), a cooling scan to 0° C. (10° C./min) and a second heating scan to 200° C. (10° C./min). The $T_m$, $T_g$, and degree of crystallinity (Xc) was determined from the second heating ramp. A reference enthalpy of melting of 93.1 J/g was used to calculate the crystallinity of PLA.

In some particular embodiments, the biodegradable ABA' triblock copolymer can be of the following formula:

(I)

wherein m and n are independently 1-2000, and in some embodiments m and n are independently 1-1000.

Formula I depicts a biodegradable ABA' triblock copolymer wherein the end blocks, i.e., A and A' blocks, each include polylactide or polylactic acid and the middle block, i.e., the B block, includes 100 mole percent of polytrimethylene carbonate and 0 mole percent polylactide or polylactic acid and the biodegradable triblock copolymer overall includes from about 15 to about 25 mole percent of the polytrimethylene carbonate and from about 75 to about 85 mole percent of the polylactide or polylactic acid.

In some embodiments, each "m" of Formula I may independently range from about 25 to about 2000. In some embodiments, each "m" of Formula I may independently range from about 50 to about 1000. In some embodiments, each "m" of Formula I may independently range from about 100 to about 500. In some embodiments, each "m" of Formula I may independently range from about 150 to about 400. In some embodiments, each "m" of Formula I may independently range from about 200 to about 300.

In some embodiments, each "m" of Formula I may independently range from about 10 to about 2000. In some embodiments, each "m" of Formula I may independently range from about 200 to about 1000. In some embodiments, each "m" of Formula I may independently range from about 300 to about 800. In some embodiments, each "m" of Formula I may independently range from about 400 to about 600.

In some embodiments, each "m" of Formula I may be the same number ranging from about 50 to about 1000. In some embodiments, each "m" of Formula I may be the same number ranging from about 100 to about 500. In embodiments, each "m" of Formula I may be the same number ranging from about 150 to about 400. In embodiments, each "m" of Formula I may be the same number ranging from about 200 to about 300.

In some embodiments, each "m" of Formula I may be the same number ranging from about 10 to about 2000. In some embodiments, each "m" of Formula I may be the same number ranging from about 200 to about 1000. In some embodiments, each "m" of Formula I may be the same number ranging from about 300 to about 800. In some embodiments, each "m" of Formula I may be the same number ranging from about 400 to about 600.

In some embodiments, "n" of Formula I may range from about 200 to about 800. In embodiments, "n" of Formula I may range from about 300 to about 700. In embodiments, "n" of Formula I may range from about 400 to about 600.

In some embodiments, each "m" of Formula I may independently range from about 100 to about 500 and "n" of Formula I may range from about 200 to about 800.

In some embodiments, each "m" of Formula I may be the same number ranging from about 100 to about 500 and "n" of Formula I may range from about 200 to about 800.

In some embodiments, each "m" of Formula I may independently range from about 150 to about 400 and "n" of Formula I may range from about 300 to about 700.

In some embodiments, each "m" of Formula I may be the same number ranging from about 150 to about 400 and "n" of Formula I may range from about 300 to about 700.

In some embodiments, each "m" of Formula I may independently range from about 200 to about 300 and "n" of Formula I may range from about 400 to about 600.

In some embodiments, each "m" of Formula I may be the same number ranging from about 200 to about 300 and "n" of Formula I may range from about 400 to about 600.

In some embodiments, "m" and "n" of Formula I are independently about 50 to about 100. In some particular embodiments, "m" of Formula I is about 70 and "n" of Formula I is about 50.

In some embodiments, the $M_n$ and $M_w$ of the triblock copolymer of Formula I are about 100,000 g/mol to about 225,000 g/mol. In some particular embodiments, the $M_n$ of the triblock copolymer of Formula I is about 100,000 g/mol to about 150,000 g/mol and the $M_w$ of the triblock copolymer of Formula I is about 150,000 g/mol to about 225,000 g/mol.

In some embodiments, the $M_n$ and $M_w$ of the triblock copolymer of Formula I are about 100,000 g/mol to about 190,000 g/mol. In some particular embodiments, the $M_n$ of the triblock copolymer of Formula I is about 100,000 g/mol to about 120,000 g/mol and the $M_w$ of the triblock copolymer of Formula I is about 170,000 g/mol to about 190,000 g/mol.

In some particular embodiments, the biodegradable ABA' triblock copolymer can be of the following formula (II)

wherein m, $n_1$ and $n_2$ are independently 1-2000, and I some embodiments 1-1000.

Formula II depicts a biodegradable ABA' triblock copolymer wherein the end blocks, i.e., A and A' blocks, each include polylactide or polylactic acid and the middle block, i.e., the B block, includes from about 55 to about 100 mole percent of polytrimethylene carbonate and 0 to about 45 mole percent polylactide or polylactic acid and the biodegradable triblock copolymer overall includes from about 15 to about 25 mole percent of the polytrimethylene carbonate and from about 75 to about 85 mole percent of the polylactide or polylactic acid.

In some embodiments, each "m" of Formula II may independently range from about 25 to about 2000. In some embodiments, each "m" of Formula II may independently range from about 50 to about 1000. In some embodiments, each "m" of Formula II may independently range from about 100 to about 500. In some embodiments, each "m" of Formula II may independently range from about 150 to about 400. In some embodiments, each "m" of Formula II may independently range from about 200 to about 300.

In some embodiments, each "m" of Formula II may independently range from about 10 to about 2000. In some embodiments, each "m" of Formula II may independently range from about 200 to about 1000. In some embodiments, each "m" of Formula II may independently range from about 300 to about 800. In some embodiments, each "m" of Formula II may independently range from about 400 to about 600.

In some embodiments, each "m" of Formula II may be the same number ranging from about 50 to about 1000. In some embodiments, each "m" of Formula II may be the same number ranging from about 100 to about 500. In embodiments, each "m" of Formula II may be the same number ranging from about 150 to about 400. In embodiments, each "m" of Formula II may be the same number ranging from about 200 to about 300.

In some embodiments, each "m" of Formula II may be the same number ranging from about 10 to about 2000. In some embodiments, each "m" of Formula II may be the same number ranging from about 200 to about 1000. In some embodiments, each "m" of Formula II may be the same number ranging from about 300 to about 800. In some embodiments, each "m" of Formula II may be the same number ranging from about 400 to about 600.

In some embodiments, "$n_1$" of Formula II may range from about 100 to about 900. In embodiments, "$n_1$" of Formula II may range from about 200 to about 800. In embodiments, "$n_1$" of Formula II may range from about 300 to about 700. In embodiments, "$n_1$" of Formula II may range from about 400 to about 600.

In some embodiments, each "m" of Formula II may independently range from about 100 to about 500 and "$n_1$" of Formula II may range from about 200 to about 800.

In some embodiments, each "m" of Formula II may be the same number ranging from about 100 to about 500 and "$n_1$" of Formula II may range from about 200 to about 800.

In some embodiments, each "m" of Formula II may independently range from about 150 to about 400 and "$n_1$" of Formula II may range from about 300 to about 700.

In some embodiments, each "m" of Formula II may be the same number ranging from about 150 to about 400 and "$n_1$" of Formula II may range from about 300 to about 700.

In some embodiments, each "m" of Formula II may independently range from about 200 to about 300 and "$n_1$" of Formula II may range from about 400 to about 600.

In some embodiments, each "m" of Formula II may be the same number ranging from about 200 to about 300 and "$n_1$" of Formula II may range from about 400 to about 600.

In some embodiments, "m" and "$n_1$" of Formula II are independently about 50 to about 100. In some particular embodiments, "m" of Formula II is about 70 and "$n_1$" of Formula II is about 50.

In some embodiments, "$n_2$" of Formula II may range from about 0 to about 405. In embodiments, "$n_2$" of Formula II may range from about 0 to about 360. In embodiments, "$n_2$" of Formula II may range from about 0 to about 315. In embodiments, "$n_2$" of Formula II may range from about 0 to about 270.

In some embodiments, "$n_2$" of Formula II may range from about 15 to about 405. In embodiments, "$n_2$" of Formula II may range from about 30 to about 360. In embodiments, "$n_2$" of Formula II may range from about 45 to about 315. In embodiments, "$n_2$" of Formula II may range from about 60 to about 270.

In some embodiments, "$n_1$" is greater than "$n_2$".
In some embodiments, "$n_1$" is greater than (2)("$n_2$").
In some embodiments, "$n_1$" is greater than (3)("$n_2$").
In some embodiments, "$n_1$" is greater than (4)("$n_2$").
In some embodiments, "m" is greater than "$n_1$" which is greater than "$n_2$".

In some embodiments, each "m" of Formula II may independently range from about 100 to about 500 and "$n_2$" of Formula II may range from about 15 to about 405.

In some embodiments, each "m" of Formula II may be the same number ranging from about 100 to about 500 and "$n_2$" of Formula II may range from about 15 to about 405.

In some embodiments, each "m" of Formula II may independently range from about 150 to about 400 and "$n_2$" of Formula II may range from about 30 to about 360.

In some embodiments, each "m" of Formula II may be the same number ranging from about 150 to about 400 and "$n_1$" of Formula II may range from about 30 to about 360.

In some embodiments, each "m" of Formula II may independently range from about 150 to about 400 and "$n_2$" of Formula II may range from about 45 to about 315.

In some embodiments, each "m" of Formula II may be the same number ranging from about 150 to about 400 and "$n_1$" of Formula II may range from about 45 to about 315.

In some embodiments, each "m" of Formula II may independently range from about 200 to about 300 and "$n_1$" of Formula II may range from about 60 to about 270.

In some embodiments, each "m" of Formula II may be the same number ranging from about 200 to about 300 and "$n_1$" of Formula II may range from about 60 to about 270.

In some embodiments, "m" and "$n_2$" of Formula II are independently about 50 to about 100. In some particular embodiments, "m" of Formula II is about 70 and "$n_2$" of Formula II is about 50.

In some embodiments, "m", "$n_1$", and "$n_2$" of Formula II are independently about 50 to about 100. In some particular embodiments, "m" and "$n_1$" of Formula II is about 70 and "$n_2$" of Formula II is about 50.

In some embodiments, "$n_1$" of Formula II may range from about 100 to about 900 and "$n_2$" of Formula II may range from about 15 to about 405, wherein "$n_1$" is greater than "$n_2$". In embodiments, "$n_1$" of Formula II may range from about 200 to about 800 and "$n_2$" of Formula II may range from about 30 to about 360, wherein "$n_1$" is greater than "$n_2$". In embodiments, "$n_1$" of Formula II may range from about 300 to about 700 and "$n_2$" of Formula II may range from about 45 to about 315, wherein "$n_1$" is greater than "$n_2$". In embodiments, "$n_1$" of Formula II may range from about 400 to about 600 and "$n_2$" of Formula II may range from about 60 to about 270, wherein "$n_1$" is greater than "$n_2$".

In some embodiments, the $M_n$ and $M_w$ of the triblock copolymer of Formula II are about 100,000 g/mol to about 225,000 g/mol. In some particular embodiments, the $M_n$ of the triblock copolymer of Formula II is about 100,000 g/mol to about 150,000 g/mol and the $M_w$ of the triblock copolymer of Formula II is about 150,000 g/mol to about 225,000 g/mol.

In some embodiments, the $M_n$ and $M_w$ of the triblock copolymer of Formula II are about 100,000 g/mol to about 190,000 g/mol. In some particular embodiments, the $M_n$ of the triblock copolymer of Formula II is about 100,000 g/mol to about 120,000 g/mol and the $M_w$ of the triblock copolymer of Formula II is about 170,000 g/mol to about 190,000 g/mol.

Forming of Triblock Copolymers

The triblock copolymers of the present disclosure can be prepared using a single or multi-step polymerization process. In embodiments, the triblock copolymers are formed using a multi-step process wherein the B block is formed in a first step and the A and A' blocks can be combined with the B block either individually in at least two different steps, or in a single step simultaneously.

One example of a multi-step process suitable for forming the ABA' triblock copolymers described herein includes a first step which includes mixing of the monomers units of the B block (e.g., monomers of lactic acid and/or trimethylene carbonate), an initiator, and a catalyst, in a dry form and under dry conditions, in a reactor. Each of the ingredients mixed are in a dry form. The reactor may include a means for mixing, such as mixing blades or magnetic stirrer. The mixing also occurs under a nitrogen atmosphere and initially at room temperature, but the temperature is increased to drive the reaction to form the B block of the triblock copolymer. After formation of the B block, at least a second step of mixing is performed wherein monomer units of the A and A' blocks (e.g., lactide monomer) and a second catalyst in dry form are mixed with the B block in the reactor to form the ABA' triblock copolymers described herein. The second step may be performed under a nitrogen atmosphere and/or while actively mixing with a mixing means. The temperature during the second step is also increased to drive the reaction. When the reaction is complete the polymer is extruded, pelletized, and dried under heat and vacuum to remove any moisture and unreacted monomer.

Any suitable initiator and/or catalyst may be used in each of the steps provided herein for forming the ABA' triblock copolymers. Some non-limiting examples of suitable initiators include diethylene glycol, triethylene glycol, tetraethylene glycol, poly(ethylene glycol), poly(propylene glycol), poly(tetramethylene glycol), and poly(caprolactone) diol. The first and second initiators may be the same or different. Some non-limiting examples of suitable catalysts include stannous chloride, stannous octoate, stannous oxide, zinc chloride and zinc oxide. In some embodiments, the initiator of the first step is diethylene glycol and the catalyst is stannous octoate. In some embodiments, the initiator of the first step is diethylene glycol and the catalyst is stannous octoate.

In another example of a multi-step process suitable for forming at least one of the ABA' triblock copolymers described herein, a mono-alcohol, such as ethanol or lactic acid, may be initially mixed with monomer units of the A block, i.e., monomers of lactic acid, with a catalyst to form the A block. Monomer units of the B block, i.e., monomers of lactic acid and/or trimethylene carbonate, may be added to the A block with a catalyst to form an A-B copolymer. Then monomer units of the A' block, i.e., monomers of lactic acid, may be added to the A-B copolymer with a catalyst to form an ABA' triblock copolymer.

Compositions

The invention further provides compositions comprising, consisting essentially of, or consisting of the triblock copolymers of the invention. Suitably, the compositions comprise, by weight, at least 1%, at least about 10%, at least about 25%, at least about 50%, at least about 75%, at least about 90%, or at least about 99% of the triblock copolymers of the invention.

For example, in addition to standing alone as a triblock copolymer, the biodegradable ABA' triblock copolymers described herein may be combined with at least one additional biocompatible material including non-biodegradable polymeric materials, biodegradable polymeric materials, and/or biologically active agents. Each of the additional biocompatible materials may suitably be present in an amount from about 0.1% to about 90%, or from about 1% to about 50%, or from about 2% to about 25%.

In the present application, "biocompatible" is understood as meaning that the materials having this property can be implanted in the human or animal body.

All biocompatible materials may be synthetic or natural, biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

Suitable biodegradable materials include, but are not limited to, polyglycolic acid (PGA), oxidized cellulose, polycaprolactone (PCL), polydioxanone (PDO, polyvinyl alcohol (PVA), polyhydroxyalkanoates (PHAs), copolymers of these compounds and mixtures thereof. The biodegradable materials may also include biopolymeric materials derived from materials such as gelatin, collagen, chitosan, keratin, elastin, cellulose, alginates, and derivatives and combinations thereof.

Suitable non-biodegradable materials include, but are not limited to, polyolefins, such as polyethylene, polypropylene, copolymers of polyethylene and polypropylene, and blends of polyethylene and polypropylene; polyamides, such as nylon; polyamines, polyimines, polyesters such as polyethylene terephthalate (PET), polytetrafluoroethylene, polyether-esters such as polybutesters, polytetramethylene ether glycol; 1,4-butanediol; polyurethanes, and combinations thereof. In embodiments, non-biodegradable materials may include silk, cotton, linen, carbon fibers, and combinations thereof. The polypropylene may be isotactic polypropylene or a mixture of isotactic and syndiotactic or atactic polypropylene.

Biologically active agents include any agent which provides a therapeutic or prophylactic effect, a compound that affects or participates in tissue growth, cell growth, and cell differentiation, a compound that may be able to invoke a biological action such as an immune response, or could play any other role in one or more biological processes.

Examples of classes of biologically active agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of these agents may be used.

Suitable antimicrobial agents which may be combined with the triblock copolymers described herein include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may also be combined with the triblock copolymers.

Other suitable biologically active agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Still other examples of suitable agents include viruses and cells, peptides, polypeptides and proteins, analogs, muteins, and active fragments thereof, such as immunoglobulins, antibodies, cytokines (e.g., lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

The additional biocompatible material may be combined with the triblock copolymers described herein in any suitable manner to form a composition suitable for forming a medical device. For example, in some embodiments, the triblock copolymer and the additional biocompatible material may be mixed to form a blend. In other embodiments, the additional biocompatible material may be bonded and/or crosslinked directly to a pendant part of the triblock copolymer described herein, wherein the ABA' triblock copolymer remains intact. For example, the additional biocompatible material may be represented by the letter "C" and may be bonded to the triblock copolymer to form a format such as, but not limited to, CABA', ABA'C, or CABA'C. Any suitable manner known to those of ordinary skill may be used to bond C to a pendant part of the ABA' triblock copolymer. Some non-limiting examples include the use of crosslinking agents, as well as the use of specific binding pairs of complimentary reactive functional groups, i.e., electrophilic/nucleophilic functional groups, or click chemistry reactive groups, such as azides and alkynes.

In some embodiments, the ABA' triblock copolymer(s) described herein may be used alone or in combination with an additional biocompatible material to form at least a portion of an implantable device, if not the entire implantable medical device.

Implantable Medical Devices

As used herein, an "implantable medical device" may be any device that can be implanted in an animal. In embodiments, the implantable medical device is made from at least one filament including at least the ABA' triblock copolymers described herein. Examples of implantable medical devices made from at least one filament include, but are not limited to, surgical sutures, surgical staples, surgical pins, surgical screws, surgical suture pledgets, surgical staple buttresses, surgical mesh, surgical plugs, vaso-occlusive devices, and combinations thereof.

In some embodiments, the biodegradable ABA' triblock copolymers described herein may be used alone or in combination with additional biocompatible materials to form a filament suitable for forming an implantable medical device. The filament may be formed using any suitable method known to those skilled in the art. Some non-limiting examples include extruding, wet-spinning, gel-spinning, electro-spinning, molding, and the like. Some additional non-limiting examples of methods suitable for forming filaments are described in U.S. Pat. Nos. 5,403,347, 5,217,485, 5,279,783, and 6,881,766, each incorporated herein by reference.

Figure 1:
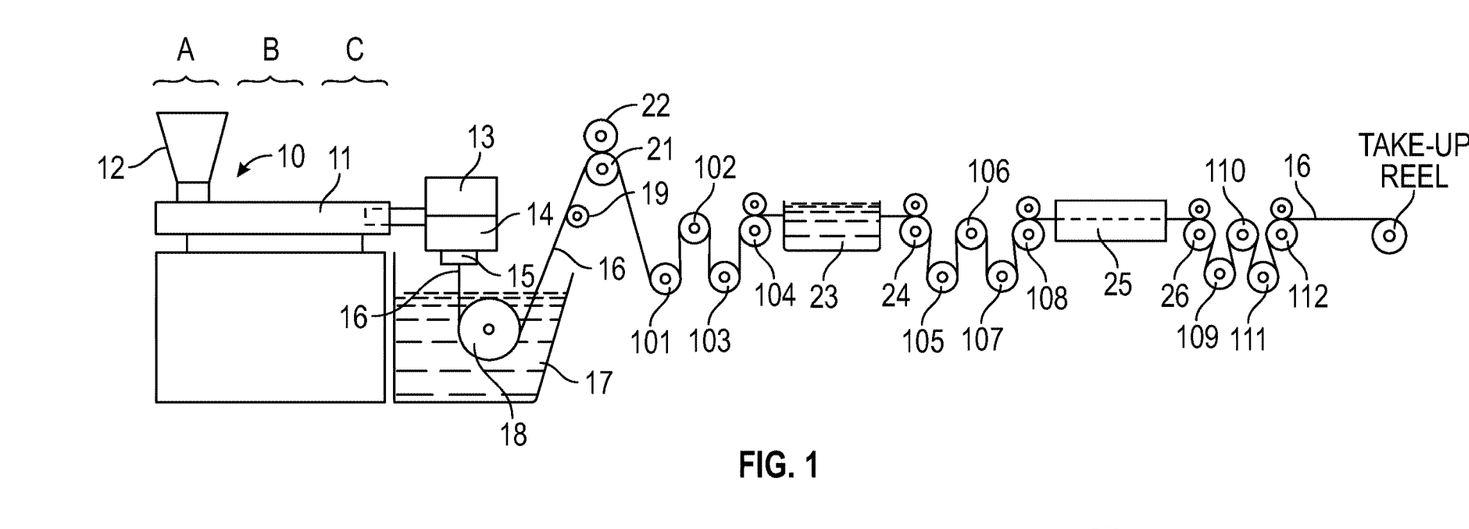
FIG. 1 is a schematic illustration of an apparatus which is suitable for manufacturing the filaments from at least one of the ABA' triblock copolymers described herein.

FIG. 1 schematically illustrates at least one format suitable for manufacturing filaments made from the biodegradable ABA' triblock copolymers described herein. Extruder unit 10 is of a known or conventional type and is equipped with controls for regulating the temperature of barrel 11 in various zones thereof. In embodiments, the temperature progressively increases in three consecutive zones A, B and C along the length of the barrel. Pellets or powder including the ABA' triblock copolymers of the present disclosure are introduced to the extruder through hopper 12. Any of the ABA' triblock copolymers described herein can be used, alone or in a composition with additional biocompatible materials.

Motor-driven metering pump 13 delivers melt extruded ABA' triblock copolymer, alone or in a composition, at a constant rate to spin pack 14 and thereafter through spinneret 15 possessing one or more orifices of desired diameter to provide a molten monofilament 16 which then enters quench bath 17, e.g., containing a cooling liquid such as water, where the monofilament solidifies.

Monofilament 16 is passed through quench bath 17 around driven roller 18 and over idle roller 19. Optionally, a wiper (not shown) may remove excess water from the monofilament as it is removed from quench bath 17. On exiting the quench bath the monofilament is wrapped around a first godet 21 provided with nip roll 22 to prevent slippage which might otherwise result from the subsequent stretching operation. The monofilament is subsequently drawn through a combination of alternating godets 101, 102, 103, 104, 105, 106, 107, 108, 109, 110, 111, and 112 and heating chambers 23 and 25 to stretch and/or anneal the monofilament into a usable form and size.

Figure 2:
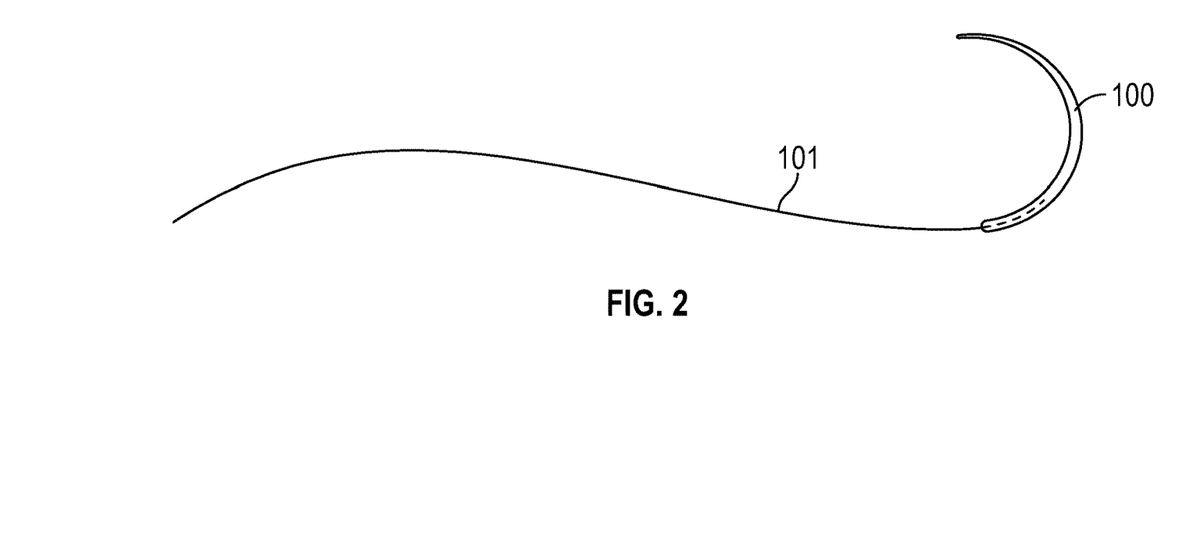
FIG. 2 is a perspective view of a suture including at least one of the ABA' triblock copolymers described herein and attached to a needle.

Filaments made from the biodegradable ABA' triblock copolymers described herein, alone or in combination with other additional biocompatible materials, can be used to form at least one of a monofilament suture, a multifilament suture, a barbed suture, an armed suture, a looped suture, a knotted suture, and the like. For example, as shown in FIG. 2, suture 101, attached on one end to needle 100, is made from at least one of the biodegradable ABA' triblock copolymers described herein, alone or in combination with other additional biocompatible materials. In embodiments, suture 101 is made solely from at least one of the biodegradable ABA' triblock copolymers described herein. The sutures described herein may be monofilament or multifilament sutures.

Figure 3:
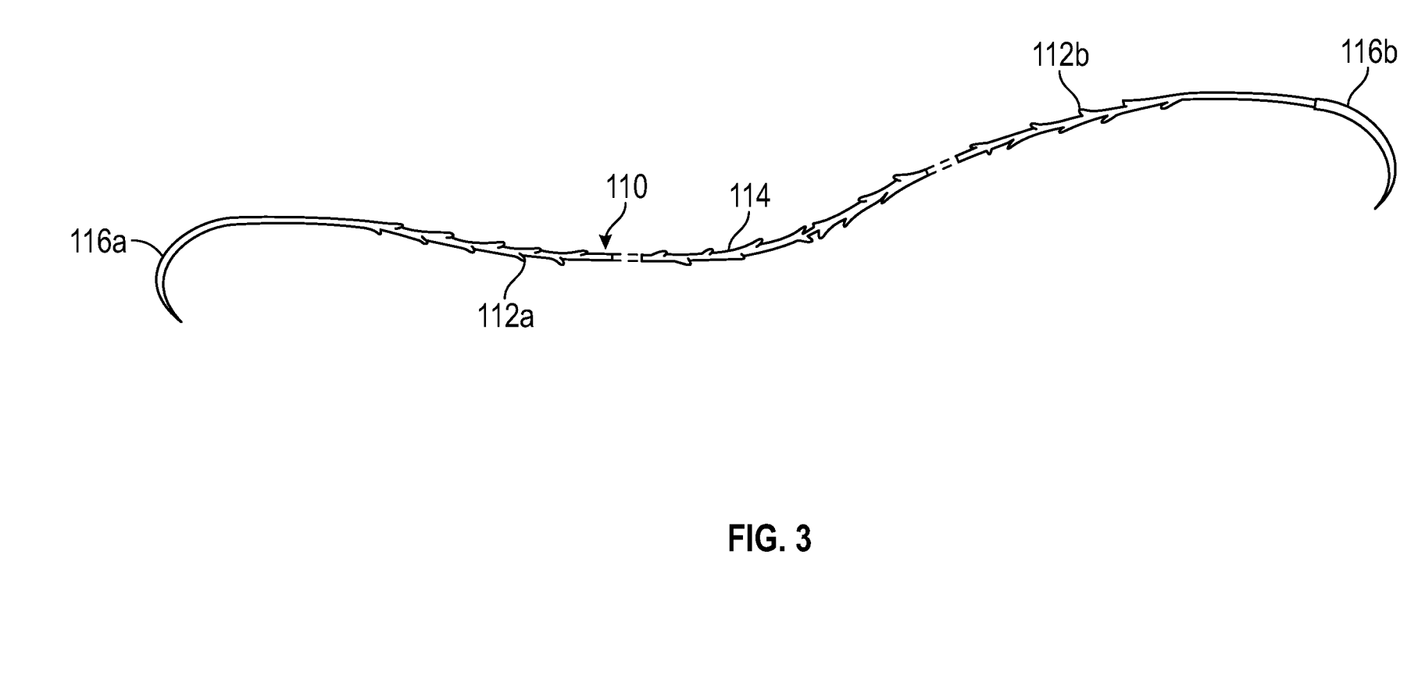
FIG. 3 is a perspective view of a barbed suture including at least one of the ABA' triblock copolymers described herein and attached to needles.

In another example, as depicted in FIG. 3, barbed suture 110, including a plurality of barbs 112 a, 112 b extending from a periphery of elongate body 114 and attached on both ends to needles 116a, 116b, is made from at least one of the biodegradable ABA' triblock copolymers described herein, alone or in combination with other additional biocompatible materials. In embodiments, barbed suture 110 is made solely from at least one of the biodegradable ABA' triblock copolymers described herein. The barbed sutures described herein may be mono-directional, bi-directional, or multi-directional barbed sutures. The barbed sutures described herein may also be monofilament or multifilament sutures.

Figure 4:
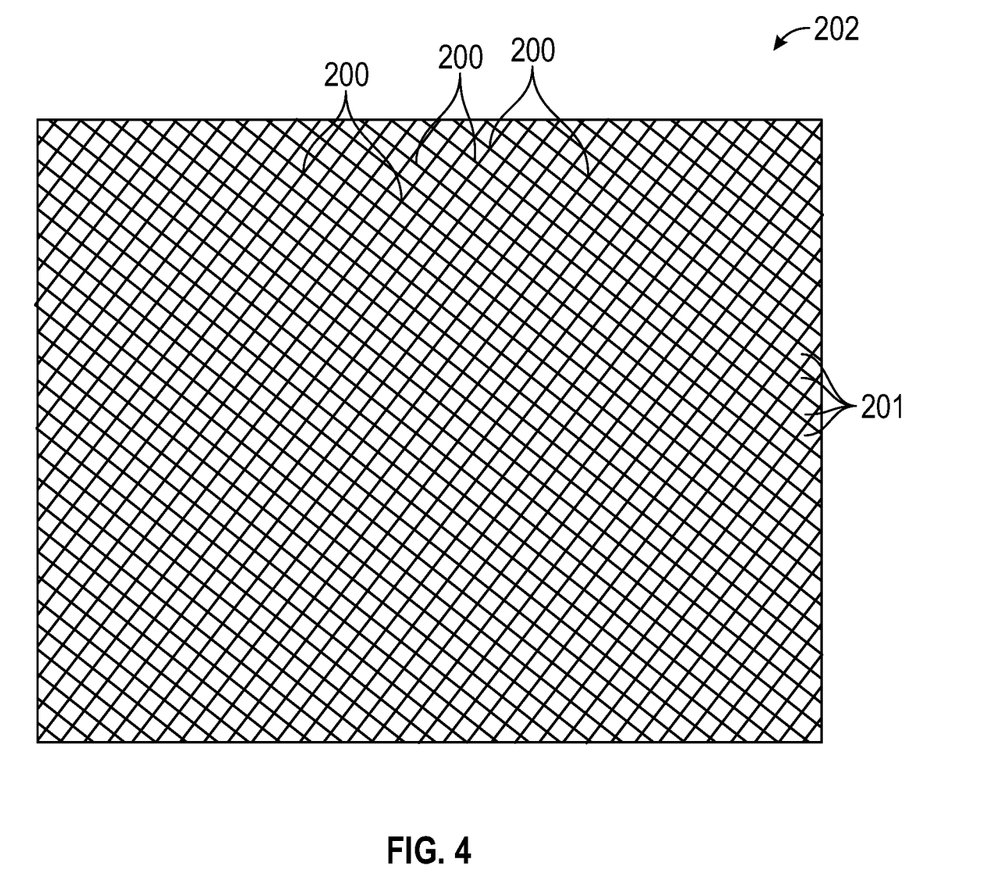
FIG. 4 is a top view of a surgical mesh including at least one of the ABA' triblock copolymers described herein.

In some embodiments, the biodegradable ABA' triblock copolymers described herein, alone or in combination with additional biocompatible materials, are used to form filaments which may be further processed to form a fabric. The fabric may be formed of interwoven filaments. The filaments may be interwoven using any suitable method including, but not limited to, braiding, weaving, knitting, and the like. The fabric may be used to form an implantable medical device such as a suture pledget, staple buttress, or surgical mesh. For example, as depicted in FIG. 4 surgical mesh 202 includes interwoven filaments 200 made from at least one of the biodegradable ABA' triblock copolymers described herein, alone or in combination with other additional biocompatible materials. In embodiments, surgical mesh 202 including filaments 200 is made solely from at least one of the biodegradable ABA' triblock copolymers described herein. The interwoven filaments 200 make pores 201 therebetween creating at least one porous surface. Although shown as rectangular, the mesh 202 may be any suitable shape and may be a two-dimensional or three-dimensional mesh. In embodiments, mesh 202 is a knit wherein the filaments 200 are knitted together to form mesh 202. The filaments 200 may be a monofilament or multifilament.

Figure 5:
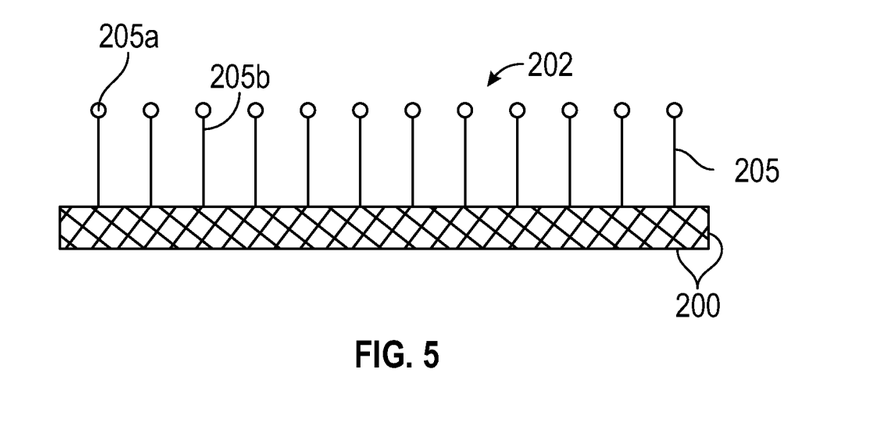
FIG. 5 is a side view of a self-gripping surgical mesh including at least one of the ABA' triblock copolymers described herein.

As shown in FIG. 5, in some embodiments the filaments described herein can be knitted together to form a self-gripping surgical mesh 203 (e.g., Progrip® mesh) including grip-members 205 such as spiked naps, which have a head 205a wider than a body 205b and are configured to attach directly to tissue and/or other mesh materials. Filaments including the triblock copolymers described herein, alone or in combination with additional biocompatible materials, can be used to form any and all elements of the self-gripping surgical mesh 203 including the grip-members 205. In embodiments, self-gripping surgical mesh 203 is made solely from the biodegradable ABA' triblock copolymers described herein. For example, the self-gripping surgical mesh may be made from a biodegradable ABA' triblock copolymer wherein the A and A' blocks are pure PLA, the B block is 0-15/85-100 mole percent PLA/TMC, and overall the biodegradable triblock copolymer is 80/20 mole percent PLA/TMC.

In embodiments, the fabric can be used to treat any type of hernia including a ventral hernia, inguinal hernia, femoral hernia, umbilical hernia, and epigastric hernia. In embodiments, the fabric can be used to treat any type of prolapse including but not limited to, bladder prolapse, rectum prolapse, small bowel prolapse, urethral prolapse, uterine prolapse, and vaginal prolapse.

Figure 6:
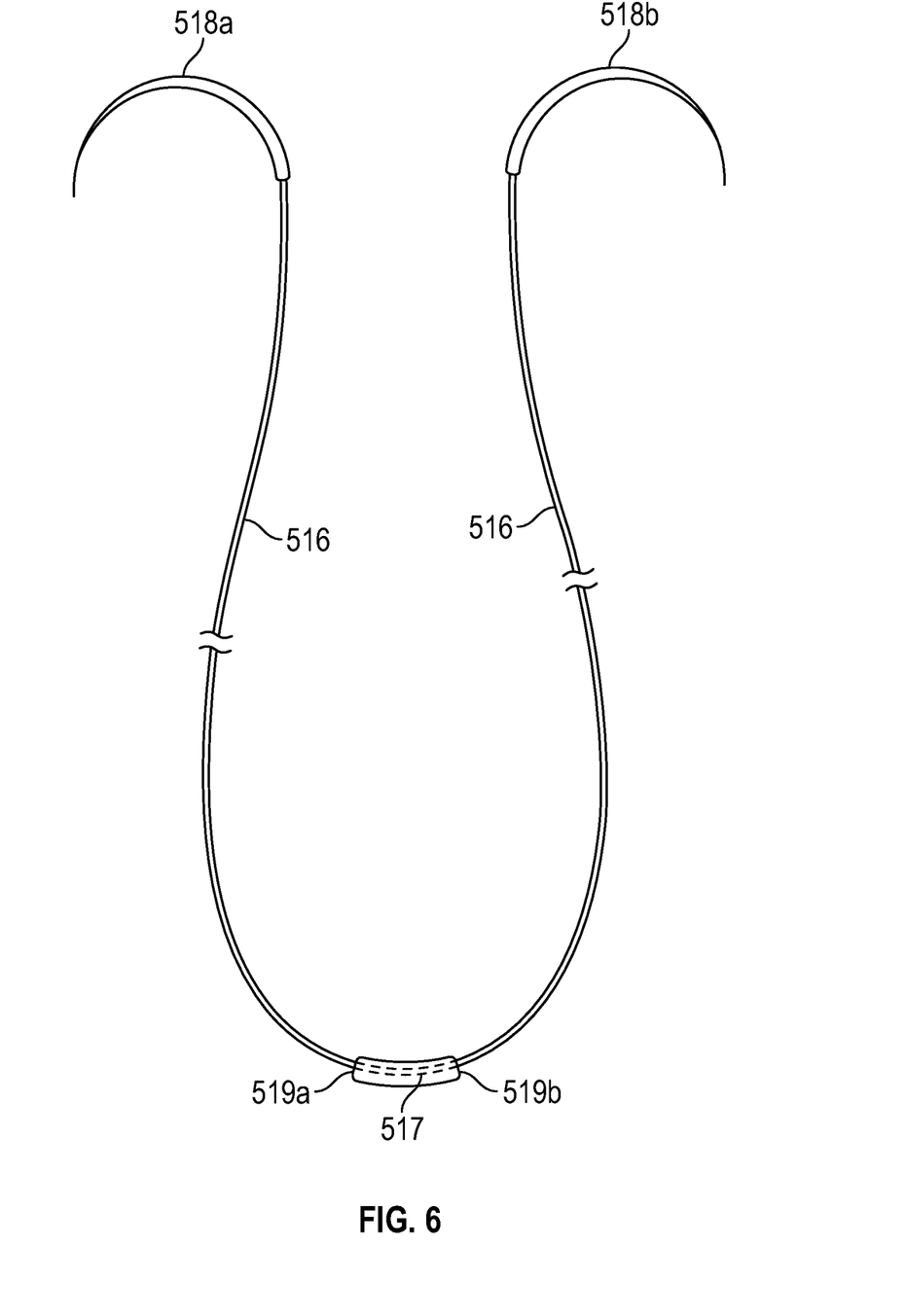
FIG. 6 is a side view of a suture pledget positioned on a double-armed suture wherein at least one of the suture pledget and suture include at least one of the ABA' triblock copolymers described herein.

As shown in FIG. 6, in some embodiments, the fabric may be used to form is a suture pledget 517, attached to a central region of suture 516 (suture/pledget junctions 519 a and 519 b illustrate where suture 516 passes through pledget 517 with the portion of suture 516 shown in phantom disposed behind pledget 517) including needles 518 a and 518b, is made from at least one of the biodegradable ABA' triblock copolymers described herein, alone or in combination with additional biocompatible materials. In embodiments, suture pledget 517 is made solely of at least one of the biodegradable ABA' triblock copolymers described herein.

In some embodiments, suture pledget 517 and suture 516 may be both made from at least one of the biodegradable ABA' triblock copolymers described herein, alone or in combination with additional biocompatible materials. In some embodiments, the suture pledget 517 and suture 516 are both made from the same biodegradable ABA' triblock copolymer. In some embodiments, the suture pledget 517 and suture 516 are both made from different biodegradable ABA' triblock copolymers described herein.

EXAMPLES

The following examples are given to aid in understanding the information provided in the present disclosure and is in no way meant to limit the scope of the present disclosure.

Example 1

Synthesis of an ABA' triblock copolymer of poly(lactic acid)-[poly(lactic acid)-poly(trimethylene carbonate)]-poly(lactic acid) (PLA-[PLA-pTMC]-PLA) including 80 mole % PLA and 20 mole % pTMC overall and the B block [PLA-pTMC] is 0 mole % PLA and 100 mole % pTMC.

In a first stage of polymerization, 5,000 g of trimethylene carbonate, 24.65 g of diethylene glycol, and 0.02% stannous octoate were added to a clean and dry stainless steel conical vessel reactor outfitted with two helicone-style mixing blades and mixed dry under a nitrogen atmosphere and at room temperature initially. The reactor temperature was increased to 180° C. and the first stage reaction monitored until formation of the B block, in the present example 100% poly(TMC), was complete.

In a second stage of polymerization, with the helicone-type mixing blades on and under a nitrogen atmosphere, 28,261 g of dry lactide monomer and 0.02% stannous octoate were added to the stainless steel conical vessel reactor including the B block from the first stage of polymerization. The reactor temperature was increased to 195° C. and the second stage reaction monitored until formation of the ABA' triblock copolymer, in the present example PLA-pTMC-PLA (PLA/pTMC 80/20 mole % overall with a B block of PLA/pTMC 0/100 mole %), was complete and removed from the reactor.

Example 2

Synthesis of an ABA' triblock copolymer of poly(lactic acid)-[poly(lactic acid)-poly(trimethylene carbonate)]-poly(lactic acid) (PLA-[PLA-pTMC]-PLA) 80 mole % PLA and 20 mole % pTMC overall, wherein the B block [PLA-pTMC] is 15 mole % PLA and 85 mole % pTMC.

In a first stage of polymerization, 5,000 g of trimethylene carbonate, 1247 g of dry L-lactide monomer, 2.75 g of diethylene glycol, and 2.90 g stannous octoate were added to a clean and dry stainless steel conical vessel reactor outfitted with two helicone-style mixing blades and mixed dry under a nitrogen atmosphere and at room temperature initially. The reactor temperature was increased to 180° C. and the first stage reaction monitored until formation of the B block, in the present example a random copolymer including 15 mole percent PLA and 85 mole percent pTMC, was complete.

In a second stage of polymerization, with the helicone-type mixing blades on and under a nitrogen atmosphere, 27,014 g of dry lactide monomer was added to the stainless steel conical vessel reactor including the B block from the first stage of polymerization. The reactor temperature was increased to 195° C. and the second stage reaction monitored until formation of the ABA' triblock copolymer, in the present example PLA-[PLA-pTMC]-PLA (PLA/pTMC 80/20 mole % overall with a B block of PLA/pTMC 15/85 mole %), was complete and removed from the reactor.

Example 3

Each of the ABA' triblock copolymers formed in Examples 1 and 2 hereinabove, as well pure PLA alone, and a few additional PLA/TMC triblock copolymers having various overall mole percentages and/or middle block mole percentages, were extruded to form filaments of various diameters. The tensile strength and molar mass of the polymeric filaments were tested in vitro to provide a degradation profile of each of the filaments. Specifically a tensile strength retention profile at 50° C. and a molar mass retention profile at 50° C. were studied. The degradation was performed in a 1/1 molar phosphate buffer at pH=7.4 at 50° C. Degradation and measurements of tensile strength and molar mass were carried out in accordance with ISO 13781: 1997 "Poly(L-lactide) resins and fabricated forms for surgical implants—in vitro degradation testing". The terms "tensile strength retention at 50° C." and "molar mass retention at 50° C." in the present specification refer to these parameters as measured by this method. Different yarn diameters between 100-150 micrometers were tested and the diameter was found to have no impact on the results (molar mass or percentage force retention). The results of the studies are depicted in FIGS. 7 and 8, respectively.

Figure 7:
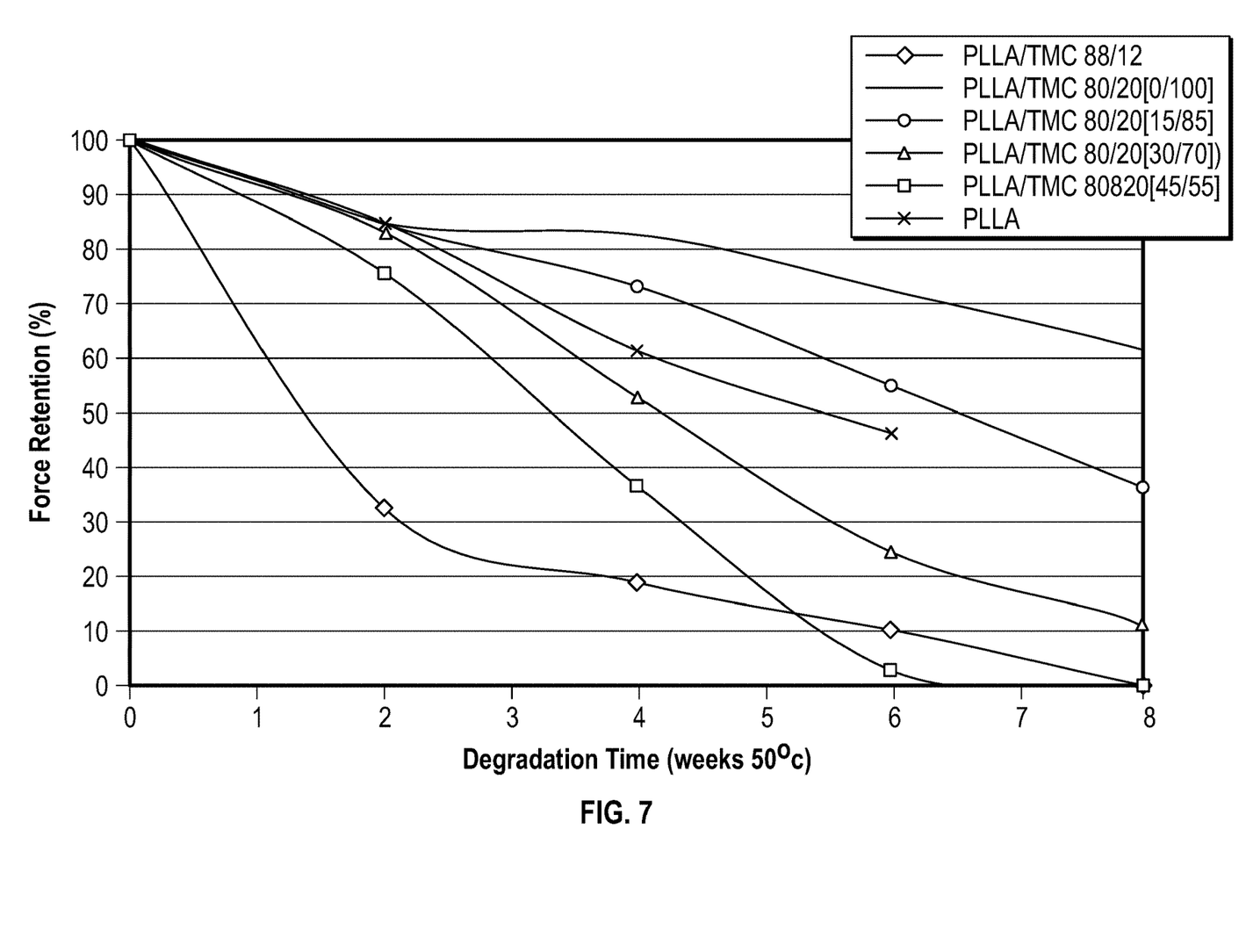
FIG. 7 is a graph of the force retention percentage compared to degradation time in weeks under of various filaments exposed to enhanced degradation conditions, some of the filaments including ABA' triblock copolymers described herein and some filaments including other comparative polymeric materials.
Figure 8:
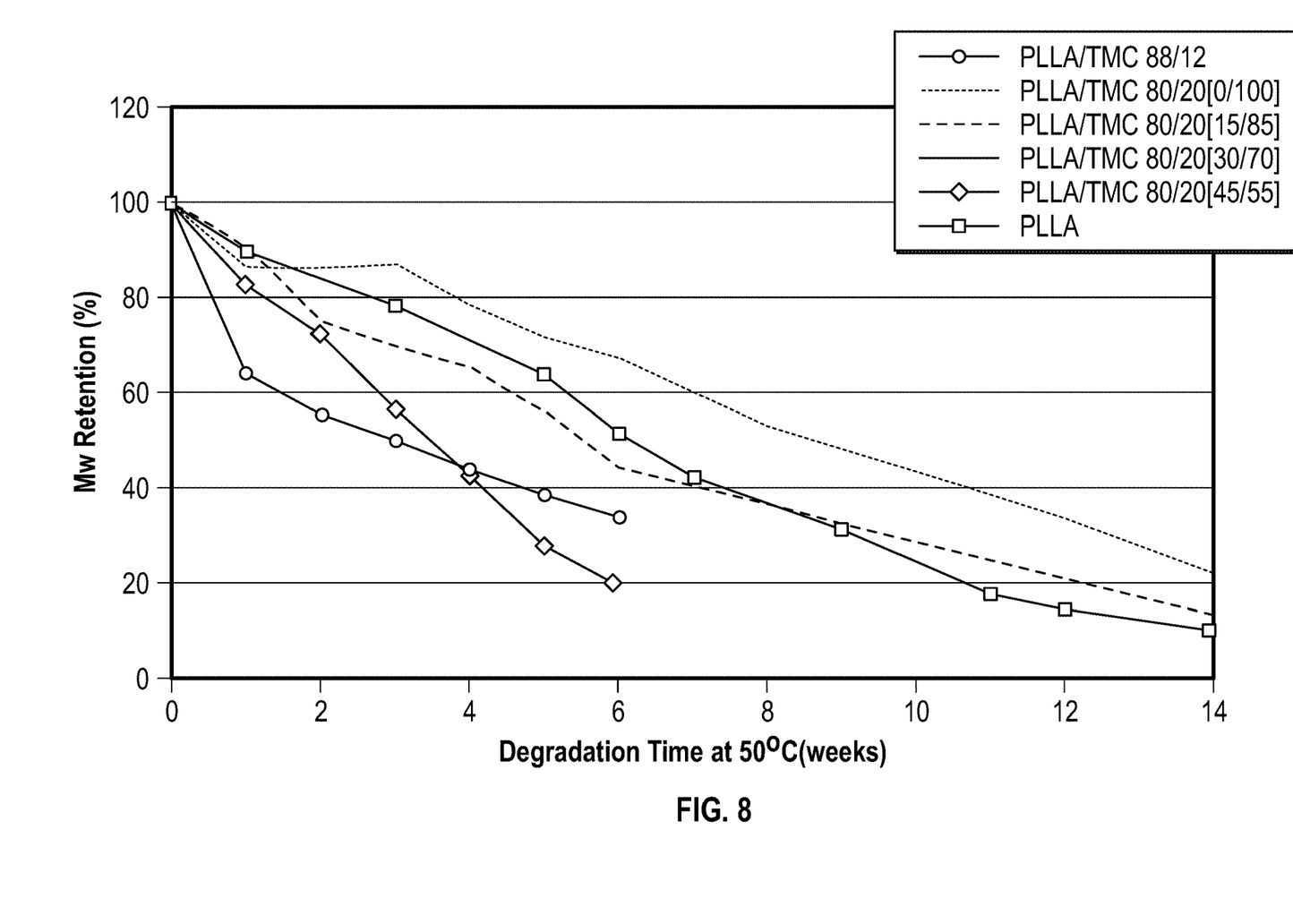
FIG. 8 is a graph of the molar mass retention percentage compared to degradation time in weeks of various filaments exposed enhanced degradation conditions, some of the fila-

As depicted in FIG. 7, the force retention (tensile strength retention) percent of the filaments made of pure PLA alone stays above 80% after about 2 weeks and maintains about 50% after about 6 weeks, but fail thereafter at 50° C. The filaments made from PLA/pTMC 80/20 [0/100] and PLA/pTMC 80/20 [15/85], i.e., non-limiting examples of ABA' triblock copolymers of the present application, display a force retention percent above 80% after about 2 weeks and maintain a force retention percent of about 50% or greater after about 6 weeks and do not fail after 6 or 8 weeks at 50° C. However, the force retention percent of the filaments made of: PLA/pTMC 80/20 [45/55] and PLA/pTMC 88/12 [0/100] drop below 80% before 2 weeks and drop well below 50% around weeks 2 and 3, respectively; and, PLA/pTMC 80/20 [30/70] drops below 50% around week 4. Additionally worth noting, the force retention percent of these three last-described filaments drops below 30% (and even 10% for 2 of these 3 filaments) by week 6, making these three last-described filaments unsuitable for providing tissue support long term, i.e., greater than 6 months and/or greater than 12 months. While the force retention percent of the filaments made from PLA/pTMC 80/20 [0/100] and PLA/pTMC 80/20 [15/85] remains greater than about 35% (and greater than about 60% for at least 1 of these 2 filaments) after 8 weeks, suggesting these filaments are suitable for providing tissue support long term, i.e., greater than 6 months and/or greater than 12 months under normal conditions.

As depicted in FIG. 2, the molar mass retention percent of the filaments made of PLA alone stays above 85% after about 1 week, stays above about 35% after about 8 weeks, and is still around about 10% after about 14 weeks. However, the filaments made from PLA/pTMC 80/20 [0/100] and PLA/pTMC 80/20 [15/85], i.e., non-limiting examples of ABA' triblock copolymers of the present application, display a molar mass retention percent above 85% after about 1 week, a molar mass retention percent of about 35% or greater after about 8 weeks, and a molar mass retention percent of about 15% or greater after about 14 weeks. While the molar mass retention percent of the filaments made of PLA/pTMC 80/20 [45/55], PLA/pTMC 80/20 [30/70], and PLA/pTMC 88/12 [0/100] drop below 85% before 1 week and fail by about week 6 and are below 35% before week 8 (about week 6).

The combination of the force retention percent and the molar mass retention percent results suggests that the ABA' triblock copolymers of the present application and/or the filaments and medical devices made therefrom are suitable for providing tissue support long term, i.e., greater than 6 months and/or greater than 12 months, without structural failure under normal conditions.

While embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

The invention claimed is:

1. An implantable surgical mesh comprising:
a plurality of interwoven filaments, at least one of the filaments including a biodegradable triblock copolymer including an A-B-A' structure wherein the A and A' blocks each include polylactide, the B block includes from about 55 to about 100 mole percent of polytrimethylene carbonate and 0 to about 45 mole percent polylactide, and the biodegradable triblock copolymer overall includes from about 15 to about 25 mole percent of the polytrimethylene carbonate and from about 75 to about 85 mole percent of the polylactide.

2. The implantable surgical mesh of claim 1, wherein the B block of includes from about 100 mole percent polytrimethylene carbonate and about 0 mole percent polylactic acid.

3. The implantable surgical mesh of claim 1, wherein the B block includes from about 55 to about 95 mole percent polytrimethylene carbonate and about 5 to about 15 mole percent polylactic acid.

4. The implantable surgical mesh of claim 1, wherein the B block includes from about 85 to about 95 mole percent polytrimethylene carbonate and about 5 to about 15 mole percent polylactic acid.

5. The implantable surgical mesh of claim 1, wherein the B block includes from about 85 mole percent polytrimethylene carbonate and about 15 mole percent polylactic acid.

6. The implantable surgical mesh of claim 1, wherein the biodegradable triblock copolymer overall includes about 20 mole percent of the polytrimethylene carbonate and about 80 mole percent of the polylactide.

7. The implantable surgical mesh of claim 1, wherein the biodegradable triblock copolymer has a weight average molecular weight (Mw) ranging from about 150,000 g/mol to about 225,000 g/mol.

8. The implantable surgical mesh of claim 1, wherein the biodegradable triblock copolymer has a number average molecular weight (Mn) ranging from about 100,000 g/mol to about 225,000 g/mol.

9. The implantable surgical mesh of claim 1, wherein the biodegradable triblock copolymer displays a melting temperature ($T_m$) ranging from about 160° C. to about 185° C.

10. The implantable surgical mesh of claim 1, wherein the biodegradable triblock copolymer displays a glass transition temperature ($T_g$) ranging from about 40° C. to about 65° C.

11. The implantable surgical mesh of claim 1, wherein the copolymer retains at least about 85% of the molecular weight after 1 week at 50° C.

12. The implantable surgical mesh of claim 1, wherein the biodegradable triblock copolymer retains at least about 35% of the molecular weight after 8 weeks at 50° C.

13. The implantable surgical mesh of claim 1, wherein the biodegradable triblock copolymer retains at least about 15% of the molecular weight after 14 weeks at 50° C.

14. The implantable surgical mesh of claim 1, wherein the at least one filament further comprises an additional biocompatible material.

15. The implantable surgical mesh of claim 1, wherein the additional biocompatible material is a biodegradable material.

16. The implantable surgical mesh of claim 1, wherein the at least one filament is a monofilament.

17. The implantable surgical mesh of claim 1, wherein the plurality of interwoven filaments are knitted together to form the implantable surgical mesh.

18. The implantable surgical mesh of claim 1, wherein the implantable surgical mesh is a two-dimensional mesh.

19. The implantable surgical mesh of claim 1, wherein the implantable surgical mesh is a three-dimensional mesh.

* * * * *